United States Patent
Vigano et al.

(10) Patent No.: US 6,599,922 B2
(45) Date of Patent: Jul. 29, 2003

(54) PROCESS FOR THE PREPARATION OF 2,5-BIS-(2,2,2-TRIFLUOROETHOXY)-N-(2-PIPERIDYLMETHYL)-BENZAMIDE (FLECAINIDE)

(75) Inventors: Enrico Vigano, Lurago d'Erba (IT); Enrica Pizzatti, Poggiridenti (IT); Renato Molteni, Inverigo (IT); Simona Lanfranconi, Montano Lucino (IT)

(73) Assignee: A.M.S.A. Anonima Materie Sintetiche e Affini S.p.A., Milan (IT)

( * ) Notice: Subject to any disclaimer, the term of this patent is extended or adjusted under 35 U.S.C. 154(b) by 0 days.

(21) Appl. No.: 10/215,588

(22) Filed: Aug. 8, 2002

(65) Prior Publication Data

US 2003/0032835 A1 Feb. 13, 2003

(30) Foreign Application Priority Data

Aug. 10, 2001 (IT) .................... MI2001A001772

(51) Int. Cl.$^7$ .................... A61K 31/4458; C07D 211/12
(52) U.S. Cl. .................... 514/331; 546/229; 546/236; 514/331
(58) Field of Search .................... 546/229, 236; 514/331

(56) References Cited

U.S. PATENT DOCUMENTS

| 3,766,247 A | 10/1973 | Mendel ..................... 260/473 |
| 3,900,481 A | * 8/1975 | Bannitt et al. ......... 260/293.77 |
| 4,005,209 A | 1/1977 | Banitt et al. ................ 424/267 |
| 4,024,175 A | 5/1977 | Satzinger et al. ........... 460/468 |

FOREIGN PATENT DOCUMENTS

| GB | 2 065 112 A | 6/1981 |
| WO | WO 99/02498 | 1/1999 |

OTHER PUBLICATIONS

Banitt, E.H. et al., "Antiarrhythmics.N–(Aminoalkylene)trifluoroethoxybenzamides and N–(Aminoalkylene) trifluoroethoxynaphthamides," *J. Med. Chem.*, 1975, 18(11): 1130–1134.

Banitt, E.H. et al., "Antiarrhythmics. 2. Synthesis and Antiarrhythmic Activity of N–(Piperidylalkyl) trifluoroethoxybenzamides)," *J. Med. Chem.*, 1977, 20(6): 821–6.

Conte, L. et al., " A New Method for Recovering Waste Alkaline Perfluoro–n–Butanesulfonate," *J. Fluorine Chem.*, 1991, 53: 277–283.

L. Conte, et al. *A New Method For Recovering Waste Alkaline Perfluoro–n–Butanesulfonate*, Journal of Fluorine Chemistry, 1991, vol. 53, pp. 277–283.

* cited by examiner

*Primary Examiner*—Alan L. Rotman
*Assistant Examiner*—Janet Coppins
(74) *Attorney, Agent, or Firm*—Morgan & Finnegan LLP

(57) ABSTRACT

Process for the synthesis of FLECAINIDE comprising the reaction between 2,5-dihydroxybenzoic acid with trifluoroethanol perfluorobutanesulphonate to give the intermediate trifluoroethanol 2,5-bis-trifluoroethoxybenzoate, the reaction of said intermediate with 2-aminomethylpiperidine to give FLECAINIDE.

17 Claims, No Drawings

PROCESS FOR THE PREPARATION OF 2,5-BIS-(2,2,2-TRIFLUOROETHOXY)-N-(2-PIPERIDYLMETHYL)-BENZAMIDE (FLECAINIDE)

FIELD OF THE INVENTION

The present invention concerns a process for the preparation of 2,5-bis-(2,2,2-trifluoroethoxy)-N-(2-piperidylmethyl)-benzamide (FLECAINIDE).

PRIOR ART

FLECAINIDE base, in general the pharmaceutically acceptable salts thereof, and in particular in hydrochloride form, is described in the U.S. Pat. No. 3,900,481. FLECAINIDE is a principal active ingredient used in human therapy as an anti-arrhythmic agent, as described in the U.S. Pat. No. 4,005,209.

The processes described in the art for the synthesis of this molecule are many. U.S. Pat. No. 4,024,175 describes the preparation of FLECAINIDE starting from 1,4-dibromobenzene transformed by reaction with trifluoroethoxyls and acetylating agents into 2,5-bis-(2,2,2-trifluoroethoxy)-acetophenone which, by oxidation (treatment with hydrochloric acid and with 2-aminomethyl-piperidine) gives FLECAINIDE.

This process, along with the others described in the art, are complex and laborious synthetic processes and, however, so as to render difficult their exploitation at the industrial size.

The need to develop new synthetic pathways, with reactions characterized by high yield, easily reproducible on an industrial scale, with high purity intermediates through the use of reagents easily commercially available, was then felt.

SUMMARY OF THE INVENTION

A new process for the preparation of FLECAINIDE, overcoming the disadvantage, inherent to the processes known in the art, has been now discovered.

The applicant has unexpectedly and surprisingly found a new process for the preparation of FLECAINIDE, as flecainide base or any one of its pharmaceutically acceptable salts, comprising the synthesis of the intermediate 2',2',2'-trifluoroethanol 2,5-bis-(2,2,2-trifluoroethoxy)benzoate by reaction of 2,5-dihydroxybenzoic acid, gentisic acid, with 2,2,2-trifluoroethanol perfluorobutanesulphonate.

The process object of the present invention is characterized by easily industrially applicable steps with high yield, starting from easily commercially available reagents, of limited costs, allowing, as a further benefit, the quantitative recovery of by-products obtained in the formation reaction of the intermediate 2',2',2'-trifluoroethanol 2,5-bis-(2,2,2-trifluoroethoxy)benzoate with considerable advantages from the industrial and environmental points of view.

DETAILED DESCRIPTION OF THE INVENTION

It is therefore an object of the present invention a FLECAINIDE preparation process, as flecainide base or any pharmaceutically acceptable salts thereof, comprising the synthesis of the intermediate 2',2',2'-trifluoroethanol 2,5-bis-(2,2,2-trifluoroethoxy)benzoate, defined as phase a) by the reaction of 2,5-dihydroxybenzoic acid with 2,2,2-trifluoroethanol perfluorobutanesulphonate in the presence of inorganic bases.

Preferably the 2,2,2-trifluoroethanol perfluorobutanesulphonate is 2,2,2-trifluoroethyl-perfluoro-n-butanesulphonate.

Preferably the molar ratio between 2,5-dihydroxybenzoic acid and 2,2,2-trifluoroethanol perfluorobutanesulphonate is comprised from 1:3 to 1:5, more preferably it is 1:3.

According to the process object of the present invention, the reaction at phase a) is preferably carried out in the presence of inorganic bases selected from the group consisting of carbonates and/or bicarbonates of sodium and/or potassium, or mixtures thereof. More preferably the base is potassium carbonate.

The reaction at phase a) is preferably carried out in oxygenated aliphatic solvents from 2 to 6 carbon atoms. The ketones from three to six carbon atoms are the most preferred. Ketones selected from the group consisting of: acetone, methylethyl-ketone, methylisobutyl-ketone are particularly preferred.

The reaction at phase a) is carried out at a temperature from 30° C. to 140° C.; the range from 50° C. to 80° C. is preferred; and the range from 50° C. to 60° C. is particularly preferred.

The perfluorobutanesulphonate alkaline salts obtained as by-products of the reaction at phase a), are recovered in a quantitative manner through their complete reconversion in 2,2,2-trifluoroethanol perfluorobutanesulphonate, which is recycled in the reaction at phase a).

The perfluorobutanesulphonate alkaline salts obtained as by-products, precipitated in the reaction mixture, are removed by filtration. Said alkaline salts are quantitatively reconverted in the 2,2,2-trifluoroethanol perfluorobutanesulphonate which is recycled in phase a).

The reconversion of the alkaline salts of perfluorobutanesulphonate in the corresponding 2,2,2-trifluoroethanol takes place according to reactions known and described in the literature as in "A new method for recovering waste alkaline perfluoro-n-butanesulphonate", Journal of fluorine chemistry, 53 (1991) 277–283. Preferably the perfluorobutanesulphonate alkaline salts are treated in lower aliphatic alcohols with gaseous mineral acids to give the corresponding perfluorobutanesulphonic acid which, after treatment with 2,2,2-trifluoroethanol in thionyl chloride, or after halogenation and successive treatment with 2,2,2-trifluoroethanol and ternary amines in aliphatic or halogenated aromatic solvents, is transformed into 2,2,2-trifluoroethanol perfluorobutanesulphonate, which is recycled in the reaction at phase a). More preferably the perfluorobutanesulphonate alkaline salts are solubilised in methanol and treated with gaseous hydrochloric acid to give the corresponding perfluorobutanesulphonic acid which, after treatment with 2,2,2-trifloroethanol in thionyl chloride, is transformed into 2,2,2-trifluoroethanol perfluorobutanesulphonate, which is recycled in the reaction at phase a); or the perfluorobutanesulphonate alkaline salts are solubilised in methanol and treated with gaseous hydrochloric acid to give the corresponding perfluorobutanesulphonic acid which, after treatment with $PCl_5$ is transformed into the corresponding perfluorobutanesulphonyl chloride, the latter reacts with 2,2,2-trifloroethanol and triethylamine in dichloromethane to give 2,2,2-trifluoroethanol perfluorobutanesulphonate, which is recycled in the reaction at phase a).

The intermediate 2',2',2'-trifluoroethanol 2,5-bis-(2,2,2-trifluoroethoxy)benzoate is easily converted into FLECAINIDE, as flecainide base or pharmaceutically acceptable salts thereof, through reactions well known in the art.

Among these reactions, constituting a particularly preferred embodiment form of the FLECAINIDE preparation process, as flecainide base or pharmaceutically acceptable salts thereof, object of the present invention, the reaction of the intermediate obtained in phase a) with 2-aminomethyl-piperidine is described. Therefore, a further object of the present invention is constituted by, as a preferred embodiment of the invention, a process which comprises, following on from phase a) the formation of the intermediate 2',2',2'-trifluoroethanol 2,5-bis-(2,2,2-trifluoroethoxy)benzoate, the reaction of said intermediate with 2-aminomethylpiperidine, said phase b), to give FLECAINIDE base.

2-aminomethyl-piperidine is an easily commercially available reagent or easily synthesized in situ, for example by catalytic hydrogenation, starting from easily available precursors, for example 2-aminomethyl-pyridine.

The reaction at phase b) is preferably carried out in aliphatic, cycloaliphatic, or aromatic solvents from one to nine carbon atoms or ethers from two to nine carbon atoms. Solvents selected from the group consisting of: heptane, hexane, cyclohexane, diethyleneglycol dimethyl ether (Diglyme), 1,2-dimethoxyethane (Glyme), toluene, xylene are the most preferred. Toluene is particularly preferred.

The reaction at phase b) is carried out at a temperature from 20° C. to 200° C.; the range of temperatures from 50° C. to 100° C. is preferred; and the range from 75° C. to 85° C. is particularly preferred.

The reaction at phase b) is carried out with a molar excess of amine. Preferably the molar ratio between the intermediate 2',2',2'-trifluoroethanol 2,5-bis-(2,2,2-trifluoroethoxy) benzoate and 2-aminomethyl-piperidine is comprised from 1:1 to 1:3, more preferably it is 1:1.15.

The FLECAINIDE base obtained, isolated by filtration from a hydroalcoholic solution of water and methanol, is easily converted into one of its pharmaceutically acceptable salts through reactions well known in the art.

Among these reactions, constituting a particularly preferred embodiment of the FLECAINIDE preparation process, as flecainide base or its pharmaceutically acceptable salts, object of the present invention, the reaction of flecainide base, obtained from phase b), with glacial acetic acid is described. Therefore, a further object of the present invention is constituted by, as a further preferred embodiment of the invention, a process which comprises, following onto phases a) and b) as described above, the reaction of flecainide base with glacial acetic acid in ethyl acetate to give flecainide monoacetate.

Flecainide monoacetate is purified by crystallisation in ethyl acetate through crystallization techniques well known in the art.

The products and the reaction intermediates have been characterized by $^1$H-NMR, Mass and HPLC analytical techniques.

The following examples are conveyed by way of indication, not of limitation, of the present invention.

EXAMPLE 1

Synthesis of Trifluoroethanol 2,5-bis Trifluoroethoxybenzoate

I)
Dissolve in 35 ml of methylethyl ketone 2.3 g (0.015 mol) of gentisic (2,5-dihydroxybenzoic) acid.

Add the potassium carbonate (6.8 g, 0.0495 mol) portionwise, wait for the precipitation of the salt and then add continuously 19.0 g of trifluoroethanol perfluorobutane-sulphonate (0.0495 mol). Reflux the suspension (80° C.) and maintain for a total of 8 hours. Eliminate the solvent at reduced pressure and dissolve the residue with 20 ml of toluene. Filter and thoroughly wash the salts with toluene. The wash is combined with the main extract. The organic phase is washed with 35 ml of water, separated, and concentrated to residue under vacuum.

Obtained 6.0 g of crude product which are used without further purification in the following stage (the theoretical expected yield is 6.0 g of intermediate).

The isolated salts are dried.

21.0 g of salts are obtained. The potassium perfluorobutanesulphonate theoretically expected is 16.7 g.

These salts are transformed into trifluorobutanesulphonic acid to recycle the reagent.

II)
Dissolve in 90 ml of acetone 6.0 g (0.039 mol) of gentisic acid. Add the potassium carbonate (17.8 g, 0.1286 mol) in portions and wait for the precipitation of the corresponding salt. Add continuously 50.0 g (0.1286 mol) of trifluoroethanol perfluorobutanesulphonate. Reflux the suspension (580°–60° C.) and maintain for approx. 12 hours. Eliminate the solvent under reduced pressure and dissolve the residue in 45 ml of toluene. Filter the salts (which are conserved) and wash them thoroughly with toluene. Combine the wash and the main extract.

Wash the toluene extract with 2×80 ml of water, separate the phases and concentrate the organic phase to residue under vacuum.

One obtains 14.2 g of amber liquid. The crude product can be used without further purification in the following step (the theoretical yield expected is 15.6 g)

The salts are dried. One obtains 51.3 g of salts.

The potassium perfluorobutanesulphonate theoretically expected is 43.5 g.

These salts are then transformed in perfluorobutanesulphonic acid for the recovery of the alkylating reagent.

EXAMPLE 2

Synthesis of Crude FLECAINIDE Base

I)
Dissolve in 48 ml of toluene 12.0 g (0.03 mol) of trifluoroethanol 2,5-bis-trifluoroethoxybenzoate. Add 3.94 g (0.0345 mol) of 2-aminomethylpiperidine and heat the solution to a temperature of 80°±5° C. for 8 hours. Cool to 50° C. and add 36 ml of water. Carry out the separation at a temperature of 45°±5° C. Concentrate the organic phase under vacuum at a temperature of 35°±5° C. so as to eliminate as much toluene as possible. A semi-solid residue is obtained which is dissolved in 20 ml of methanol and concentrated again to a residue under vacuum. Methanol (40 ml) is then added and heated with refluxing until a yellow solution is obtained. Then cool until the crude base crystallizes, the precipitation is completed by adding 40 ml of water.

The temperature of the suspension is adjusted to 50°±5° C. for 2 hours, then filter and wash with water.

11.1 g of dry crude flecainide base is obtained with an HPLC purity ≧99% (the theoretical expected yield is 12.4 g of base).

EXAMPLE 3

Synthesis of Perfluorobutanesulphonic Acid

I)
25 g (0.074 mol) of potassium perfluorobutanesulphonate are suspended in 63 ml of methanol. The suspension is heated to a temperature of 50° C. and at the same time hydrochloric acid gas is bubbled through for approx. 1 hour. At the end of the addition the suspension is cooled to a temperature of 0°±5° C. and the potassium chloride filtered. The solution is concentrated under vacuum so as to eliminate the solvent. 26.5 g of a yellowish residue is obtained with a titre of 79.63% equal to 21.1 g of perfluorobutanesulphonic acid (Expected theoretical yield 22.21 g).

EXAMPLE 4

Synthesis of Trifluoroethanol Perfluorobutanesulphonate

I)

To a solution of trifluoroethanol (1.05 g, 0.0105 mol) in anhydrous ethyl ether (20 ml) is added dropwise 0.011 mol of triethylamine without the temperature exceeding 30° C., then cooled to a temperature of −30° C. and 0.01 mol of perfluorobutanesulphonylfluoride slowly added. It is allowed to return to room temperature and to stir overnight. The solution is poured into 100 g of ice/water. The phases are separated, the organic phase is dried over sodium sulphate. The ether is evaporated at atmospheric pressure, the residue is distilled at reduced pressure (47°–47.5° C. at 17–18 mm Hg). The pure ester is obtained with yields of 50–55%.

II)

A solution of 21.0 g of trifluoroethanol (0.210 mol) in 300 ml of anhydrous dichloromethane is cooled to a temperature of 0°/+5° C., the triethanolamine (22.2 g, 0.220 mol) is added dropwise maintaining a temperature of +5° C.

At the end of the addition the temperature of the solution is adjusted to −5°±5° C. with saline and, maintaining the temperature below 0° C., over the course of 2 hours (61.0 g, 0.200 mol) perfluorobutanesulphonylfluoride is added dropwise. This is left overnight at a temperature of −5°±5° C. under continuous stirring.

The solution is poured into 100 g of ice/water. The phases are separated, the organic phase is dried over sodium sulphate.

The solvent is evaporated under vacuum, the residue is distilled at reduced pressure (T=47°–47.5° C. at 17–18 mm Hg).

55.3 g of pure ester is obtained with a yield of 72% of the theoretical.

What is claimed is:

1. Process for the preparation of FLECAINIDE, as flecainide base or any pharmaceutically acceptable salts thereof, comprising the synthesis of the intermediate 2',2',2'-trifluoroethanol 2,5-bis-(2,2,2-trifluoroethoxy)benzoate, defined as phase a), by the reaction of 2,5-dihydroxybenzoic acid with 2,2,2-trifluoroethanol perfluorobutanesulphonate in the presence of inorganic bases.

2. The process according to claim 1, wherein the 2,2,2-trifluoroethanol perfluorobutanesulphonate is 2,2,2-trifluoroethyl-perfluoro-n-butanesulphonate.

3. The process according to claim 1, wherein the molar ratio between 2,5-dihydroxybenzoic acid and 2,2,2-trifluoroetanolo perfluorobutanesulphonate is comprised from 1:3 to 1:5.

4. The process according to claim 3, wherein the molar ratio is 1:3.

5. The process according to claim 1, wherein the reaction in phase a) is preferably carried out in the presence of inorganic bases selected from the group consisting of carbonates and/or bicarbonates of sodium and/or potassium, or mixtures thereof.

6. The process according to claim 5, wherein the base is potassium carbonate.

7. The process according to claim 1, wherein the reaction at phase a) is carried out in oxygenated aliphatic solvents from 2 to 6 carbon atoms.

8. The process according to claim 7, wherein the solvents are ketones from 3 to 6 carbon atoms.

9. The process according to claim 8, wherein the ketones are selected from the group consisting of: acetone, methylethyl ketone, methylisobutyl ketone or mixtures thereof.

10. The process according to claim 1, wherein the reaction at phase a) is carried out at a temperature from 30° C. to 140° C.

11. The process according to claim 1, wherein the perfluorobutanesulphonate alkaline salts obtained as by-products from the reaction in phase a), are recovered in a quantitative manner through their complete reconversion into 2,2,2-trifluoroethanol perfluorobutanesulphonate, which is recycled in the reaction at phase a).

12. The process according to claim 11, wherein the perfluorobutanesulphonate alkaline salts are treated in lower aliphatic alcohols with gaseous mineral acids giving the corresponding perfluorobutanesulphonic acid which, after treatment with 2,2,2-trifluoroethanol in thionyl chloride, or after halogenation and successive treatment with 2,2,2-trifluoroethanol and ternary amines in aliphatic or halogenated aromatic solvents, is transformed into 2,2,2-trifluoroethanol perfluorobutanesulphonate, which is recycled in the reaction at phase a).

13. The process according to claim 12, wherein the perfluorobutanesulphonate alkaline salts are solubilised in methanol and treated with gaseous hydrochloric acid to give the corresponding perfluorobutanesulphonic acid which, after treatment with 2,2,2-trifluoroethanol in thionyl chloride, is transformed into 2,2,2-trifluoroethanol perfluorobutanesulphonate, which is recycled in the reaction at phase a).

14. The process according to claim 12, wherein the perfluorobutanesulphonate alkaline salts are solubilised in methanol and treated with gaseous hydrochloric acid to give the corresponding perfluorobutanesulphonic acid which, after treatment with $PCl_5$ is transformed into the corresponding perfluorobutanesulphonyl chloride, the latter reacts with 2,2,2-trifluoroethanol and triethylamine in dichloromethane to give 2,2,2-trifluoroethanol perfluorobutanesulphonate, which is recycled in the reaction at phase a).

15. The process according to claim 1, further comprising following onto phase a) of formation of the intermediate 2',2',2'-trifluoroethanol 2,5-bis-(2,2,2-trifluoroethoxy)benzoate by the reaction of 2,5-dihydroxybenzoic acid with 2,2,2-trifluoroethanol perfluorobutanesulphonate in the presence of inorganic bases, the reaction of the intermediate 2',2',2'-trifluoroethanol 2,5-bis-(2,2,2-trifluoroethoxy)benzoate with 2-aminomethyl-piperdine, said phase b), to give FLECAINIDE base.

16. The process according to claim 10, wherein the temperature is from 50° C. to 80° C.

17. The process according to claim 16, wherein the temperature is from 50° C. to 60° C.

* * * * *

UNITED STATES PATENT AND TRADEMARK OFFICE
CERTIFICATE OF CORRECTION

PATENT NO.    : 6,599,922 B2
DATED         : July 29, 2003
INVENTOR(S)   : Vigano et al.

It is certified that error appears in the above-identified patent and that said Letters Patent is hereby corrected as shown below:

Column 5,
Line 3, replace "trifluoroetanolo" with -- trifluoroethanol --.

Column 6,
Line 2, delete ":" and replace "ketone or" with -- ketone and --.

Signed and Sealed this

Twenty-ninth Day of June, 2004

JON W. DUDAS
*Acting Director of the United States Patent and Trademark Office*